United States Patent [19]
Pafford et al.

[11] Patent Number: 5,698,502
[45] Date of Patent: Dec. 16, 1997

[54] POLYOL ESTER COMPOSITIONS WITH UNCONVERTED HYDROXYL GROUPS FOR USE AS LUBRICANT BASE STOCKS

[75] Inventors: Bernie J. Pafford, Berkeley Heights; Jeenok T. Kim, Holmdel; Patrick E. Godici, Millington; Haven S. Aldrich, Annandale; Richard H. Schlosberg, Bridgewater, all of N.J.; Martin A. Krevalis, Baton Rouge, La.

[73] Assignee: Exxon Chemical Patents Inc, Houston, Tex.

[21] Appl. No.: 712,023

[22] Filed: Sep. 11, 1996

[51] Int. Cl.$^6$ .................. C10M 105/40; C10M 129/76
[52] U.S. Cl. .............................. 508/485; 508/519
[58] Field of Search ................................. 508/485

[56] References Cited

U.S. PATENT DOCUMENTS

| | | | |
|---|---|---|---|
| 3,115,519 | 12/1963 | Crouse et al. | 560/263 |
| 3,441,600 | 4/1969 | Chao et al. | 508/485 |
| 4,049,563 | 9/1977 | Burrous | 508/209 |
| 4,053,491 | 10/1977 | Koch et al. | 554/227 |
| 4,113,635 | 9/1978 | Sakurai et al. | 508/312 |
| 4,144,183 | 3/1979 | Koch et al. | 508/485 |
| 4,175,047 | 11/1979 | Schick et al. | 508/485 |
| 4,178,261 | 12/1979 | Dhein et al. | 508/485 |
| 4,234,497 | 11/1980 | Honig | 508/485 |
| 4,292,187 | 9/1981 | Hentschel et al. | 508/455 |
| 4,336,176 | 6/1982 | Lindner | 524/310 |
| 4,362,636 | 12/1982 | Small, Jr. | 508/501 |
| 4,370,248 | 1/1983 | Horodysky et al. | 508/198 |
| 4,421,886 | 12/1983 | Worschech et al. | 524/310 |
| 4,440,657 | 4/1984 | Metro et al. | 508/282 |
| 4,504,385 | 3/1985 | Keys | 252/61 |
| 4,614,604 | 9/1986 | Helfert et al. | 524/308 |
| 4,734,211 | 3/1988 | Kennedy | 508/501 |
| 4,753,743 | 6/1988 | Sech | 508/314 |
| 4,764,296 | 8/1988 | Kennedy | 508/400 |
| 4,812,248 | 3/1989 | Marwick | 508/485 |
| 4,820,431 | 4/1989 | Kennedy | 508/501 |
| 4,938,881 | 7/1990 | Ripple et al. | 508/237 |
| 4,957,649 | 9/1990 | Ripple et al. | 508/237 |
| 4,959,169 | 9/1990 | McGraw et al. | 252/68 |
| 5,057,247 | 10/1991 | Schmid et al. | 508/481 |
| 5,064,546 | 11/1991 | Dasai | 508/436 |
| 5,185,092 | 2/1993 | Fukuda et al. | 508/440 |
| 5,211,884 | 5/1993 | Bunemann et al. | 508/485 |
| 5,273,672 | 12/1993 | Dasai et al. | 508/495 |
| 5,374,303 | 12/1994 | van Hoorn | 106/38.22 |
| 5,403,503 | 4/1995 | Seiki et al. | 508/440 |
| 5,447,563 | 9/1995 | van Hoorn | 106/38.22 |
| 5,547,597 | 8/1996 | Koganei et al. | 508/485 |

FOREIGN PATENT DOCUMENTS

| | | |
|---|---|---|
| 854728 | 9/1960 | Canada . |
| 458584 | 5/1990 | European Pat. Off. . |
| 0 573 231 | 5/1993 | European Pat. Off. . |
| 05017790-A | 7/1991 | Japan . |

*Primary Examiner*—Ellen M. McAvoy
*Attorney, Agent, or Firm*—Richard D. Jordan

[57] ABSTRACT

A synthetic ester composition which exhibits thermal and oxidative stability, lower friction coefficient and lower wear, wherein the ester composition comprises the reaction product of: a linear or branched alcohol having the general formula $R(OH)_n$, wherein R is an aliphatic or cyclo-aliphatic group having from about 2 to 20 carbon atoms and n is at least 2; and at least one linear and/or branched acid which has a carbon number in the range between about $C_4$ to $C_{20}$, wherein the synthetic ester composition has a hydroxyl number of between about greater than 5 to 180, preferably between about greater than 5 to 100, and more preferably between about 10 to 80.

34 Claims, 5 Drawing Sheets

POLYOL ESTER COMPOSITIONS WITH UNCONVERTED HYDROXYL GROUPS FOR USE AS LUBRICANT BASE STOCKS

The present invention generally relates to polyol ester compositions which exhibit enhanced thermal/oxidative stability, lower friction coefficient, reduced sediment formation, and lower wear compared to conventional fully esterified synthetic esters. In particular, the unique polyol esters of the present invention have unconverted hydroxyl groups from the reaction product of a polyol with a branched and/or linear acid, thereby allowing the unconverted hydroxyl groups to be used to substantially delay the onset of oxidative degradation versus fully esterified polyol esters. The present invention also reduces or eliminates the amount of antioxidant which is required to attain an acceptable level of thermal/oxidative stability based upon a given amount of polyol ester. This ester composition is particularly useful as a base stock for fully formulated lubricating oils, such as aircraft turbine oils.

BACKGROUND OF THE INVENTION

Lubricants in commercial use today are prepared from a variety of natural and synthetic base stocks admixed with various additive packages and solvents depending upon their intended application. The base stocks typically include mineral oils, highly refined mineral oils, poly alpha olefins (PAO), polyalkylene glycols (PAG), phosphate esters, silicone oils, diesters and polyol esters.

Stability requirements and the accompanying need for lubricating oils with greater stability have been increasing. As engines become smaller and tighter, and engine operating temperatures go higher, the need for higher stability lubricants has increased. In addition, higher stability lubricants which retain this feature are also desired when longer drain intervals and decreased maintenance are desired, both of which result in savings.

In end uses where higher stability is desired or required, fully esterified polyol esters have been commonly used due to their high thermal and oxidative stability. One of the most demanding lubricant applications in terms of thermal and oxidative requirements is aircraft turbine oils (ATO). Polyol esters have been commonly used as base stocks in aircraft turbine oils. Despite their inherent thermal/oxidative stability as compared with other base stocks (e.g., mineral oils, poly alpha olefins, etc.), even these synthetic ester lubricants are subject to oxidative degradation and cannot be used, without further modification, for long periods of time under oxidizing conditions. It is known that this degradation is related to oxidation and/or hydrolysis of the ester base stock.

Conventional synthetic polyol ester aircraft turbine oil formulations require the addition of antioxidants (also known as oxidation inhibitors). Antioxidants reduce the tendency of the ester base stock to deteriorate in service where deterioration can be evidenced by the products of oxidation such as sludge and varnish-like deposits on the metal surfaces, and by acidity growth and, in some instances, increased viscosity. Such antioxidants include arylamines (e.g., dioctyl diphenylamine and phenyl-alpha-naphthylamine), and the like.

Frequently replacing the aircraft turbine oil or adding an antioxidant thereto to suppress oxidation increases the total cost of maintaining aircraft turbines. It would be most desirable to have an ester base stock which exhibits substantially enhanced thermal/oxidative stability compared to conventional synthetic ester base stocks, and wherein the ester base stock does not require frequent replacement due to decomposition (i.e., oxidative degradation). It would also be economically desirable to eliminate or reduce the amount of antioxidant which is normally added to such lubricant base stocks.

Upon thermal/oxidative stress a weak carbon hydrogen bond is cleaved resulting in an unstable carbon radical on the ester. The role of conventional antioxidants is to transfer a hydrogen atom to the unstable carbon radical and effect a "healing" of the radical. The following equations demonstrate the effect of antioxidants (AH):

or

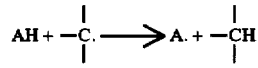

The antioxidant molecule is convened into a radical, but this radical (A.) is far more stable than that of the ester-based system. Thus, the effective lifetime of the ester is extended. When the added antioxidant is consumed, the ester radicals are not healed and irreversible oxidative degradation of the polyol ester composition occurs. One measure of relative thermal/oxidative stability well known in the art is the use of high pressure differential scanning calorimetry (HPDSC).

HPDSC has been used to evaluate the thermal/oxidative stabilities of formulated automotive lubricating oils (see J. A. Walker, W. Tsang, SAE 801383), for synthetic lubricating oils (see M. Wakakura, T. Sato, Journal of Japanese Petroleum Institute, 24 (6), pp. 383–392 (1981)) and for polyol ester derived lubricating oils (see A. Zeeman, Thermochim, Acta, 80(1984)1). In these evaluations, the time for the bulk oil to oxidize was measured which is the induction time. Longer induction times have been shown to correspond to oils having higher antioxidant concentrations or correspond to oils having more effective antioxidants or at a fixed level of a given antioxidant, have been shown to correspond to oils having intrinsically more stable base stocks. For automotive lubricants, higher induction times have been correlated with viscosity break point times.

The use of HPDSC as described herein provides a measure of stability through oxidation induction times. A polyol ester can be blended with a constant amount of dioctyl diphenylamine which is an antioxidant. This fixed amount of antioxidant provides a constant level of protection for the polyol ester base stock against bulk oxidation. Thus, oils tested in this manner with longer induction times have greater intrinsic resistance to oxidation. For the higher hydroxyl esters according to the present invention to which no antioxidant has been added, the longer induction times reflect the greater stability of the base stock by itself and also the natural antioxidancy of the esters due to the free hydroxyl group.

The present inventors have developed a unique polyol ester composition having enhanced thermal/oxidative stability when compared to conventional synthetic polyol ester compositions. This was accomplished by synthesizing a polyol ester composition from a polyol and branched and/or linear acid in such a way that it may have a substantial amount of unconverted hydroxyl groups. Having —CHROH functional groups bonded to the ester backbone is believed to allow these higher hydroxyl esters to cause the thermal/oxidative stability of the novel polyol ester composition to increase, as measured by high pressure differential scanning calorimetry (HPDSC). That is, these novel polyol ester compositions provide a pathway capable of scavenging alkoxide and alkyl peroxide radicals, thereby reducing the rate at which oxidative degradation can occur.

The thermal and oxidative stability which is designed into the novel polyol ester compositions of the present invention eliminates or reduces the level of antioxidant which must be added to a particular lubricant to achieve a given level of stability and stability retention, thereby providing a substantial cost savings to lubricant manufacturers. In addition, the degree of esterification (as measured by hydroxyl number) must be controlled to a critical range to eliminate the tendency of the partially esterified base stock from becoming too corrosive and/or too viscous for the equipment it is being used to lubricate. Also, the present inventors have discovered that only a minimal amount of additional unconverted hydroxyl groups need to be present in order to achieve large cleanliness credits.

With molar conversions in excess of 99%, nearly all the free hydroxyl groups have been converted in the ester base stocks used in current lubricating oils. One common analytical technique used to monitor conversion is hydroxyl number. Hydroxyl number measures the free hydroxyl groups by determining the amount of acetic anhydride that the sample will react with under certain conditions. Anhydride is introduced in excess with the sample. Once the reaction is complete, the remaining anhydride is determined by titration with a basic solution. The hydroxyl number is reported as milligrams of KOH per gram of the sample. A standard method for measuring hydroxyl number is detailed by the American Oil Chemist's Society as A.O.C.S. Cd 13–60. For highly converted esters, the hydroxyl number is generally less than or equal to 5.

Hydroxyl number is a convenient method for determining how close an esterification reaction is to completion. However, due to differences in the molecular weights of the acids, hydroxyl numbers for various esters can differ for the same conversion.

Therefore, the present inventors have discovered that incorporating somewhat higher hydroxyl number polyol ester base stocks into formulated oils, e.g., formulated aircraft turbine oils, will exhibit the following enhanced properties versus oils formulated from fully esterified polyol esters: (1) improved thermal and oxidative stability in the liquid phase; (2) comparable thermal and oxidative stability in the vapor phase; and (3) no corrosion debit was observed. The present inventors have also discovered that polyol ester base stocks having higher hydroxyl numbers (i.e., greater than 5) have an optimum performance when the hydroxyl numbers remain within the critical ranges set forth hereafter with respect to sediment formation as demonstrated via the oxidation/corrosion stability (OC&S) data to follow.

The present invention also provides many additional advantages which shall become apparent as described below.

SUMMARY OF THE INVENTION

A synthetic ester composition exhibiting thermal and oxidative stability which comprises the reaction product of: a branched or linear alcohol having the general formula $R(OH)_n$, wherein R is an aliphatic or cyclo-aliphatic group having from about 2 to 20 carbon atoms and n is at least 2; and at least one branched and/or linear acid which has a carbon number in the range between about $C_4$ to $C_{20}$; wherein the synthetic ester composition has a hydroxyl number between about greater than 5 to 180 depending upon the acid and polyol used (e.g., 1to 25% unconverted hydroxyl groups, based on the total amount of hydroxyl groups in the branched or linear alcohol), preferably between about greater than 5 to 100 (e.g., 1 to 15% unconverted hydroxyl groups), and more preferably between about 10–80 (e.g., 2 to 10% unconverted hydroxyl groups).

The resultant synthetic polyol ester composition according to the present invention can exhibit a thermal/oxidative stability measured by HPDSC at 220° C., 3.445 MPa air and 0.5 wt. % Vanlube® 81 antioxidant (i.e., V-81 which is a dioctyl diphenyl amine) of greater than about 25 minutes, preferably greater than about 30, and most preferably greater than about 40 minutes.

Optionally, a diacid may be used to form either a complex alcohol ester (only if a second alcohol is also used) or a complex acid ester which also exhibits the enhanced thermal and oxidative stability properties so long as the hydroxyl number thereof is within the prescribed range.

Optionally, an antioxidant is present in an amount of between about 0 to 8 wt. %, based on the synthetic polyol ester composition, more preferably, between about 0.01 to 4.0 wt. %.

The present invention also includes a formulated lubricant (e.g., an aircraft turbine oil) which is prepared from at least one synthetic polyol ester composition having a hydroxyl number in the range between about greater than 5 to 180, and a lubricant additive package. The aircraft turbine oil formulation preferably comprises about 85–100% by weight of the synthetic polyol ester composition and about 0 to 15% by weight the additive package. Optionally, a diluent may be added to the formulation in an amount between about 0–30%, wherein the polyol ester is reduced to 55–100%.

The additive package may comprise at least one additive selected from the group consisting of: anti-foaming agents, anti-wear agents, corrosion inhibitors, hydrolytic stabilizers, metal deactivators, detergents, pour point depressants, viscosity improvers, viscosity index improvers, and oxidation inhibitors.

Still other formulated oils can be formed according to the present invention by blending this unique high hydroxyl synthetic polyol ester composition and at least one additional base stock selected from the group consisting of: mineral oils, highly refined mineral oils, poly alpha olefins, polyalkylene glycols, phosphate esters, silicone oils, diesters and polyol esters. The synthetic polyol ester composition is blended with at least one additional base stock in a ratio of between about 99:1 mole % to 1:99 mole % of high hydroxyl synthetic polyol ester to additional base stock.

The present invention also involves a process for preparing a synthetic ester composition which comprises the steps of reacting a branched or linear polyol with at least one branched and/or linear acid, wherein the synthetic ester composition exhibits a hydroxyl number in the range between about greater than 5 to 180, with or without an esterification catalyst, at a temperature in the range between about 140° to 250° C. and a pressure in the range between about 30 mm Hg to 760 mm Hg (3.999 to 101.308 kPa) for about 0.1 to 12 hours, preferably 1 to 8 hours. The product is then treated in a contact process step by contacting it with a solid such as, for example, alumina, zeolite, activated carbon, clay, etc.

DESCRIPTION OF THE PREFERRED EMBODIMENTS

Figure 1:
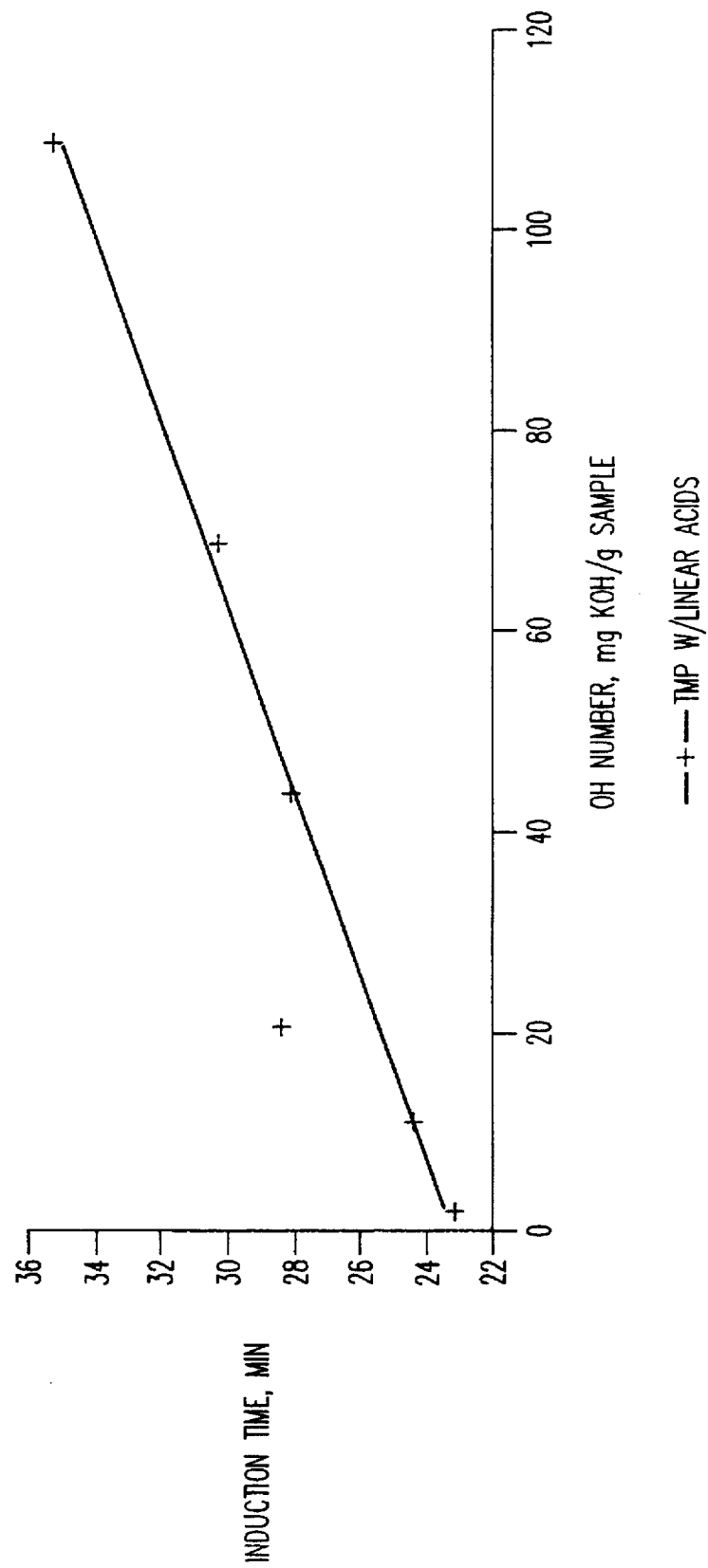
FIG. 1 is a graph demonstrating the impact of hydroxyl number on induction times (with antioxidant) using the HPDSC test.

The polyol ester composition of the present invention is preferably formed by reacting a polyhydroxyl compound with at least one branched and/or linear acid. The composition of the feed polyol and acid is adjusted so as to provide the desired composition of the product ester.

The high hydroxyl esters formed in accordance with the present invention are typically resistant to high temperature oxidation with or without the use of conventional antioxidants such as V-81.

The acid is preferably either a branched or linear acid such that the unconverted hydroxyl groups which are bonded to the resultant ester composition act similarly to an antioxidant such that it transfers a hydrogen atom to the unstable carbon radical which is produced when the ester molecule is under thermal stress, thereby effecting a "healing" of the radical (i.e., convert the carbon radical to a stable alcohol and oxygen). These unconverted hydroxyl groups which act as internal antioxidants, can substantially reduce or, in some instances, eliminate the need for the addition of costly antioxidants to the polyol ester composition. Moreover, esters having unconverted hydroxyl groups bonded thereto demonstrate substantially enhanced thermal/oxidative stability versus esters having similar amounts of antioxidants admixed therewith.

The fact that polyol esters having unconverted hydroxyl groups also exhibit lower end friction coefficients and wear volume than similar fully esterified polyol esters, suggests that these polyol esters can also be used as anti-wear agents or friction modifiers.

Alternatively, a mixture of linear and branched acids can be reacted with the branched or linear alcohol as set forth immediately above to produce an ester base stock exhibiting higher thermal and oxidative stability so long as the reaction product has a hydroxyl number in the range between greater than about 5 to 180, preferably greater than about 5 to 100, most preferably between about 10–80.

The esterification reaction is preferably conducted, with or without a catalyst, at a temperature in the range between about 140° to 250° C. and a pressure in the range between about 30 mm Hg to 760 mm Hg (3.999 to 101.308 kPa) for about 0.1 to 12 hours, preferably 1 to 8 hours. The stoichiometry in the reactor is variable, with the capability of vacuum stripping unreacted acid to generate the preferred final composition.

If the esterification reaction is conducted under catalytic conditions, then the preferred esterification catalysts are titanium, zirconium and tin catalysts such as titanium, zirconium and tin alcoholates, carboxylates and chelates. Selected acid catalysts may also be used in this esterification process. See U.S. Pat. No. 5,324,853 (Jones et al.), which issued on Jun. 28, 1994, and U.S. Pat. No. 3,056,818 (Werber), which issued on Oct. 2, 1962, both of which are incorporated herein by reference.

ALCOHOLS

Among the alcohols which can be reacted with the branched acid and/or linear acid are, by way of example, polyols (i.e., polyhydroxyl compounds) represented by the general formula:

$$R(OH)_n$$

wherein R is any aliphatic or cyclo-aliphatic hydrocarbyl group (preferably an alkyl) and n is at least 2. The hydrocarbyl group may contain from about 2 to about 20 or more carbon atoms, and the hydrocarbyl group may also contain substituents such as chlorine, nitrogen and/or oxygen atoms. The polyhydroxyl compounds generally may contain one or more oxyalkylene groups and, thus, the polyhydroxyl compounds include compounds such as polyetherpolyols. The number of carbon atoms (i.e., carbon number, wherein the term carbon number as used throughout this application refers to the total number of carbon atoms in either the acid or alcohol as the case may be) and number of hydroxyl groups contained in the polyhydroxyl compound used to form the carboxylic esters may vary over a wide range.

The following alcohols are particularly useful as polyols: neopentyl glycol, 2,2-dimethylol butane, trimethylol ethane, trimethylol propane, trimethylol butane, monopentaerythritol, technical grade pentaerythritol, di-pentaerythritol, tri-pentaerythritol, ethylene glycol, propylene glycol and polyalkylene glycols (e.g., polyethylene glycols, polypropylene glycols, polybutylene glycols, etc., and blends thereof such as a polymerized mixture of ethylene glycol and propylene glycol). The most preferred alcohols are technical grade (e.g., approximately 88% mono-, 10% di- and 1–2% tri-pentaerythritol) pentaerythritol, monopentaerythritol, di-pentaerythritol, neopentyl glycol and trimethylol propane.

BRANCHED ACIDS

The branched acid is preferably a mono-carboxylic acid which has a carbon number in the range between about $C_4$ to $C_{20}$, more preferably about $C_7$ to $C_{10}$ wherein methyl or ethyl branches are preferred. The mono-carboxylic acid is preferably at least one acid selected from the group consisting of: 2,2- dimethyl propionic acid (neopentanoic acid), neoheptanoic acid, neooctanoic acid, neononanoic acid, isohexanoic acid, neodecanoic acid, 2-ethyl hexanoic acid (2EH), 3,5,5-trimethyl hexanoic acid (TMH), isoheptanoic acid, isooctanoic acid, isononanoic acid and isodecanoic acid. One especially preferred branched acid is 3,5,5-trimethyl hexanoic acid. The term "neo" as used herein refers to a trialkyl acetic acid, i.e, an acid which is triply substituted at the alpha carbon with alkyl groups. These alkyl groups are equal to or greater than $CH_3$ as shown in the general structure set forth herebelow:

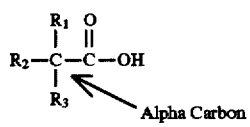

wherein $R_1$, $R_2$, and $R_3$ are greater than or equal to $CH_3$ and not equal to hydrogen.

3,5,5-trimethyl hexanoic acid has the structure set forth herebelow:

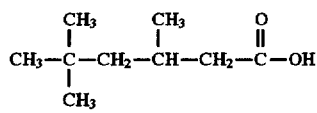

LINEAR ACIDS

The preferred mono-carboxylic linear acids are any linear saturated alkyl carboxylic acid having a carbon number in the range between about $C_4$ to $C_{20}$, preferably $C_5$ to $C_{10}$.

Some examples of linear acids include n-pentanoic, n-hexanoic, n-heptanoic, n-octanoic, n-nonanoic, and n-decanoic acids.

If it is desired to form a complex alcohol ester or complex acid ester than it is desirable that the synthetic ester composition according to the present invention also include a polybasic acid selected from the group consisting of: any $C_2$ to $C_{12}$ polybasic acids, e.g., adipic, azelaic, sebacic and dodecanedioic acids.

The reaction product from Equation 1 above can either be used by itself as a synthetic polyol ester base stock or in admixture with other base stocks, such as mineral oils, highly refined mineral oils, poly alpha olefins (PAO), polyalkylene glycols (PAG) phosphate esters, silicone oils, diesters and polyol esters. It is preferable to blend in a ratio of between about 99:1 mole % to 1:99 mole % of high hydroxyl synthetic polyol ester to additional base stock.

The present invention also encompasses higher hydroxyl complex esters which exhibit enhanced thermal/oxidative stability. Complex acid esters are made via the reaction of a polyol, a monocarboxylic acid, and a polybasic acid (such as adipic acid). Compared to typical polyol esters (i.e., polyol and monocarboxylic acid), complex acid esters have higher viscosities, due to the formation of dimers, trimers, and other oligomers. As with polyol esters, complex acid esters are typically prepared in a process that results in a high conversion of the polyol moieties.

The polyol ester composition according to the present invention is particularly useful in the formulation of lubricating oils. The lubricating oils contemplated for use with the polyol ester compositions of the present invention include both mineral and synthetic hydrocarbon oils of lubricating viscosity and mixtures thereof with other synthetic oils. The synthetic hydrocarbon oils include long chain alkanes such as cetanes and olefin polymers such as oligomers of 1-hexene, 1-octene, 1-decene, and 1-dodecene, etc. The other synthetic oils include (1) fully esterified ester oils, with no free hydroxyls, such as pentaerythritol esters of monocarboxylic acids having 4 to 20 carbon atoms, trimethylol propane esters of monocarboxylic acids having 4 to 20 carbon atoms, (2) polyacetals and (3) siloxane fluids. Especially useful among the synthetic esters are those made from polybasic acids and monohydric alcohols. Also useful are the ester fluids made by fully esterifying pentaerythritol, or mixtures thereof with di- and tri-pentaerythritol, with an aliphatic monocarboxylic acid containing from 1 to 20 carbon atoms, or mixtures of such acids.

The formulated lubricant according to the present invention preferably comprises about 85–100% by weight of at least one polyol ester composition of the present invention and about 0 to 15% by weight lubricant additive package. Alternatively, the base stock could comprise at least one additional base stock selected from the group consisting of: mineral oils, highly refined mineral oils, alkylated mineral oils, poly alpha olefins, polyalkylene glycols, phosphate esters, silicone oils, diesters and polyol esters.

The lubricant is preferably one selected from the group consisting of: crankcase engine oils, two-cycle engine oils, catapult oils, hydraulic fluids, drilling fluids, turbine oils (e.g., aircraft turbine oils), greases, compressor oils, gear oils and functional fluids.

CRANKCASE LUBRICATING OILS

The polyol ester composition can be used in the formulation of crankcase lubricating oils (i.e., passenger car motor oils, heavy duty diesel motor oils, and passenger car diesel oils) for spark-ignited and compression-ignited engines. The additives listed below are typically used in such amounts so as to provide their normal attendant functions. Typical amounts for individual components are also set forth below. All the values listed are stated as mass percent active ingredient.

| ADDITIVE | MASS % (Broad) | MASS % (Preferred) |
| --- | --- | --- |
| Ashless Dispersant | 0.1–20 | 1–8 |
| Metal detergents | 0.1–15 | 0.2–9 |
| Corrosion Inhibitor | 0–5 | 0–1.5 |
| Metal dihydrocarbyl dithiophosphate | 0.1–6 | 0.1–4 |
| Supplemental anti-oxidant | 0–5 | 0.01–1.5 |
| Pour Point Depressant | 0.01–5 | 0.01–1.5 |
| Anti-Foaming Agent | 0–5 | 0.001–0.15 |
| Supplemental Anti-wear Agents | 0–0.5 | 0–0.2 |
| Friction Modifier | 0–5 | 0–1.5 |
| Viscosity Modifier | 0.01–15 | 0–10 |
| Synthetic and/or Mineral Base Stock | Balance | Balance |

The individual additives may be incorporated into a base stock in any convenient way. Thus, each of the components can be added directly to the base stock by dispersing or dissolving it in the base stock at the desired level of concentration. Such blending may occur at ambient temperature or at an elevated temperature.

Preferably, all the additives except for the viscosity modifier and the pour point depressant are blended into a concentrate or additive package described herein as the additive package, that is subsequently blended into base stock to make finished lubricant. Use of such concentrates is conventional. The concentrate will typically be formulated to contain the additive(s) in proper amounts to provide the desired concentration in the final formulation when the concentrate is combined with a predetermined amount of base lubricant.

The concentrate is preferably made in accordance with the method described in U.S. Pat. No. 4,938,880. That patent describes making a pre-mix of ashless dispersant and metal detergents that is pre-blended at a temperature of at least about 100° C. Thereafter, the pre-mix is cooled to at least 85° C. and the additional components are added.

The final crankcase lubricating oil formulation may employ from 2 to 20 mass % and preferably 5 to 10 mass %, typically about 7 to 8 mass % of the concentrate or additive package with the remainder being base stock.

The ashless dispersant comprises an oil soluble polymeric hydrocarbon backbone having functional groups that are capable of associating with particles to be dispersed. Typically, the dispersants comprise amine, alcohol, amide, or ester polar moieties attached to the polymer backbone often via a bridging group. The ashless dispersant may be, for example, selected from oil soluble salts, esters, aminoesters, amides, imides, and oxazolines of long chain hydrocarbon substituted mono and dicarboxylic acids or their anhydrides; thiocarboxylate derivatives of long chain hydrocarbons; long chain aliphatic hydrocarbons having a polyamine attached directly thereto; and Mannich condensation products formed by condensing a long chain substituted phenol with formaldehyde and polyalkylene polyamine.

The viscosity modifier (VM) functions to impart high and low temperature operability to a lubricating oil. The VM used may have that sole function, or may be multifunctional.

Multifunctional viscosity modifiers that also function as dispersants are also known. Suitable viscosity modifiers are polyisobutylene, copolymers of ethylene and propylene and higher alpha-olefins, polymethacrylates, polyalkylmethacrylates, methacrylate copolymers, copolymers of an unsaturated dicarboxylic acid and a vinyl compound, inter polymers of styrene and acrylic esters, and partially hydrogenated copolymers of styrene/isoprene, styrene/butadiene, and isoprene/butadiene, as well as the partially hydrogenated homopolymers of butadiene and isoprene and isoprene/divinylbenzene.

Metal-containing or ash-forming detergents function both as detergents to reduce or remove deposits and as acid neutralizers or rust inhibitors, thereby reducing wear and corrosion and extending engine life. Detergents generally comprise a polar head with long hydrophobic tail, with the polar head comprising a metal salt of an acid organic compound. The salts may contain a substantially stoichiometric amount of the metal in which they are usually described as normal or neutral salts, and would typically have a total base number (TBN), as may be measured by ASTM D-2896 of from 0 to 80. It is possible to include large amounts of a metal base by reacting an excess of a metal compound such as an oxide or hydroxide with an acid gas such a such as carbon dioxide. The resulting overbased detergent comprises neutralized detergent as the outer layer of a metal base (e.g., carbonate) micelle. Such overbased detergents may have a TBN of 150 or greater, and typically from 250 to 450 or more.

Detergents that may be used include oil-soluble neutral and overbased sulfonates, phenates, sulfurized phenates, thiophosphonates, salicylates, and naphthenates and other oil-soluble carboxylates of a metal, particularly the alkali or alkaline earth metals, e.g., sodium, potassium, lithium, calcium, and magnesium. The most commonly used metals are calcium and magnesium, which may both be present in detergents used in a lubricant, and mixtures of calcium and/or magnesium with sodium. Particularly convenient metal detergents are neutral and overbased calcium sulfonates having TBN of from 20 to 450 TBN, and neutral and overbased calcium phenates and sulfurized phenates having TBN of from 50 to 450.

Dihydrocarbyl dithiophosphate metal salts are frequently used as anti-wear and antioxidant agents. The metal may be an alkali or alkaline earth metal, or aluminum, lead, tin, molybdenum, manganese, nickel or copper. The zinc salts are most commonly used in lubricating oil in amounts of 0.1 to 10, preferably 0.2 to 2 wt. %, based upon the total weight of the lubricating oil composition. They may be prepared in accordance with known techniques by first forming a dihydrocarbyl dithiophosphoric acid (DDPA), usually by reaction of one or more alcohol or a phenol with $P_2S_5$ and then neutralizing the formed DDPA with a zinc compound. For example, a dithiophosphoric acid may be made by reacting mixtures of primary and secondary alcohols. Alternatively, multiple dithiophosphoric acids can be prepared where the hydrocarbyl groups on one are entirely secondary in character and the hydrocarbyl groups on the others are entirely primary in character. To make the zinc salt any basic or neutral zinc compound could be used but the oxides, hydroxides and carbonates are most generally employed. Commercial additives frequently contain an excess of zinc due to use of an excess of the basic zinc compound in the neutralization reaction.

Oxidation inhibitors or antioxidants reduce the tendency of base stocks to deteriorate in service where deterioration can be evidenced by the products of oxidation such as sludge and varnish-like deposits on the metal surfaces and by viscosity growth. Such oxidation inhibitors include hindered phenols, alkaline earth metal salts of alkylphenolthioesters having preferably $C_5$ to $C_{12}$ alkyl side chains, calcium nonylphenol sulfide, ashless oil soluble phenates and sulfurized phenates, phosphosulfurized or sulfurized hydrocarbons, phosphorous esters, metal thiocarbamates, oil soluble copper compounds as described in U.S. Pat. No. 4,867,890, and molybdenum containing compounds.

Friction modifiers may be included to improve fuel economy. Oil-soluble alkoxylated mono- and di-amines are well known to improve boundary layer lubrication. The amines may be used as such or in the form of an adduct or reaction product with a boron compound such as a boric oxide, boron halide, metaborate, boric acid or a mono-, di- or tri-alkyl borate.

Other friction modifiers are known. Among these are esters formed by reacting carboxylic acids and anhydrides with alkanols. Other conventional friction modifiers generally consist of a polar terminal group (e.g. carboxyl or hydroxyl) covalently bonded to an oleophillic hydrocarbon chain. Esters of carboxylic acids and anhydrides with alkanols are described in U.S. Pat. No. 4,702,850. Examples of other conventional friction modifiers are described by M. Belzer in the "Journal of Tribology" (1992), Vol. 114, pp. 675–682 and M. Belzer and S. Jahanmir in "Lubrication Science" (1988), Vol. 1, pp. 3–26. One such example is organo-metallic molybdenum.

Rust inhibitors selected from the group consisting of nonionic polyoxyalkylene polyols and esters thereof, polyoxyalkylene phenols, and anionic alkyl sulfonic acids may be used.

Copper and lead bearing corrosion inhibitors may be used, but are typically not required with the formulation of the present invention. Typically such compounds are the thiadiazole polysulfides containing from 5 to 50 carbon atoms, their derivatives and polymers thereof. Derivatives of 1,3,4 thiadiazoles such as those described in U.S. Pat. Nos. 2,719,125; 2,719,126; and 3,087,932; are typical. Other similar materials are described in U.S. Pat. Nos. 3,821,236; 3,904,537; 4,097,387; 4,107,059; 4,136,043; 4,188,299; and 4,193,882. Other additives are the thio and polythio sulfenamides of thiadiazoles such as those described in GB-1560830. Benzotriazoles derivatives also fall within this class of additives. When these compounds are included in the lubricating composition, they are preferably present in an amount not exceeding 0.2 wt % active ingredient.

A small amount of a demulsifying component may be used. A preferred demulsifying component is described in EP-330522. It is obtained by reacting an alkylene oxide with an adduct obtained by reacting a bis-epoxide with a polyhydric alcohol. The demulsifier should be used at a level not exceeding 0.1 mass % active ingredient. A treat rate of 0.001 to 0.05 mass % active ingredient is convenient.

Pour point depressants, otherwise known as lube oil flow improvers, lower the minimum temperature at which the fluid will flow or can be poured. Such additives are well known. Typical of those additives which improve the low temperature fluidity of the fluid are $C_8$ to $C_{18}$ dialkyl fumarate/vinyl acetate copolymers, polyalkylmethacrylates and the like.

Foam control can be provided by many compounds including an antifoamant of the polysiloxane type, for example, silicone oil or polydimethyl siloxane.

Some of the above-mentioned additives can provide a multiplicity of effects; thus for example, a single additive may act as a dispersant-oxidation inhibitor. This approach is well known and does not require further elaboration.

TWO-CYCLE ENGINE OILS

The polyol ester composition can be used in the formulation of two-cycle engine oils together with selected lubricant additives. The preferred two-cycle engine oil is typically formulated using the polyol ester composition formed according to the present invention together with any conventional two-cycle engine oil additive package. The additives listed below are typically used in such amounts so as to provide their normal attendant functions. The additive package may include, but is not limited to, viscosity index improvers, corrosion inhibitors, oxidation inhibitors, coupling agents, dispersants, extreme pressure agents, color stabilizers, surfactants, diluents, detergents and rust inhibitors, pour point depressants, antifoaming agents, and anti-wear agents.

The two-cycle engine oil according to the present invention can employ typically about 75 to 85% base stock, about 1to 5% solvent, with the remainder comprising an additive package.

Examples of the above additives for use in lubricants are set forth in the following documents which are incorporated herein by reference: U.S. Pat. No. 4,663,063 (Davis), which issued on May 5, 1987; U.S. Pat. No. 5,330,667 (Tiffany, III et al.), which issued on Jul. 19, 1994; U.S. Pat. No. 4,740,321 (Davis et al.), which issued on Apr. 26, 1988; U.S. Pat. No. 5,321,172 (Alexander et al.), which issued on Jun. 14, 1994; and U.S. Pat. No. 5,049,291 (Miyaji et al.), which issued on Sep. 17, 1991.

CATAPULT OILS

Catapults are instruments used on aircraft carriers at sea to eject the aircraft off of the carrier. The polyol ester composition can be used in the formulation of catapult oils together with selected lubricant additives. The preferred catapult oil is typically formulated using the polyol ester composition formed according to the present invention together with any conventional catapult oil additive package. The additives listed below are typically used in such amounts so as to provide their normal attendant functions. The additive package may include, but is not limited to, viscosity index improvers, corrosion inhibitors, oxidation inhibitors, extreme pressure agents, color stabilizers, detergents and rust inhibitors, antifoaming agents, anti-wear agents, and friction modifiers. These additives are disclosed in Klamann, "Lubricants and Related Products", *Verlag Chemie*, Deerfield Beach, Fla., 1984, which is incorporated herein by reference.

The catapult oil according to the present invention can employ typically about 90 to 99% base stock, with the remainder comprising an additive package.

HYDRAULIC FLUIDS

The polyol ester composition can be used in the formulation of hydraulic fluids together with selected lubricant additives. The preferred hydraulic fluids are typically formulated using the polyol ester composition formed according to the present invention together with any conventional hydraulic fluid additive package. The additives listed below are typically used in such amounts so as to provide their normal attendant functions. The additive package may include, but is not limited to, oxidation inhibitors, viscosity index improvers, corrosion inhibitors, boundary lubrication agents, demulsifiers, pour point depressants, and antifoaming agents.

The hydraulic fluid according to the present invention can employ typically about 90 to 99% base stock, with the remainder comprising an additive package.

Other additives are disclosed in U.S. Pat. No. 4,783,274 (Jokinen et al.), which issued on Nov. 8, 1988, and which is incorporated herein by reference.

DRILLING FLUIDS

The polyol ester composition can be used in the formulation of drilling fluids together with selected lubricant additives. The preferred drilling fluids are typically formulated using the polyol ester composition formed according to the present invention together with any conventional drilling fluid additive package. The additives listed below are typically used in such amounts so as to provide their normal attendant functions. The additive package may include, but is not limited to, viscosity index improvers, corrosion inhibitors, wetting agents, water loss improving agents, bactericides, and drill bit lubricants.

The drilling fluid according to the present invention can employ typically about 60 to 90% base stock and about 5 to 25% solvent, with the remainder comprising an additive package. See U.S. Pat. No. 4,382,002 (Walker et al), which issued on May 3, 1983, and which is incorporated herein by reference.

Suitable hydrocarbon solvents include: mineral oils, particularly those paraffin base oils of good oxidation stability with a boiling range of from 200°–400° C. such as Mentor 28®, sold by Exxon Chemical Americas, Houston, Tex.; diesel and gas oils; and heavy aromatic naphtha.

TURBINE OILS

The polyol ester composition can be used in the formulation of turbine oils, especially aircraft turbine oils, together with selected lubricant additives. The preferred turbine oil is typically formulated using the polyol ester composition formed according to the present invention together with any conventional turbine oil additive package. The additives listed below are typically used in such amounts so as to provide their normal attendant functions. The additive package may include, but is not limited to, corrosion inhibitors, oxidation inhibitors, thickeners, anti-wear agents, extreme pressure agents, and hydrolytic stabilizers.

The turbine oil according to the present invention can employ typically about 85 to 100% base stock, with the remainder comprising an additive package.

GREASES

The polyol ester composition can be used in the formulation of greases together with selected lubricant additives. The main ingredient found in greases is the thickening agent or gellant and differences in grease formulations have often involved this ingredient. Besides, the thickener or gellants, other properties and characteristics of greases can be influenced by the particular lubricating base stock and the various additives that can be used.

The preferred greases are typically formulated using the polyol ester composition formed according to the present invention together with any conventional grease additive package. The additives listed below are typically used in such amounts so as to provide their normal attendant functions. The additive package may include, but is not limited to, viscosity index improvers, oxidation inhibitors, extreme pressure agents, detergents and rust inhibitors, pour point depressants, metal deactivators, anti-wear agents, and thickeners or gellants.

The grease according to the present invention can employ typically about 80 to 95% base stock and about 5 to 20% thickening agent or gellant, with the remainder comprising an additive package.

Typical thickening agents used in grease formulations include the alkali metal soaps, clays, polymers, asbestos, carbon black, silica gels, polyureas and aluminum complexes. Soap thickened greases are the most popular with lithium and calcium soaps being most common. Simple soap greases are formed from the alkali metal salts of long chain fatty acids with lithium 12-hydroxystearate, the predominant one formed from 12-hydroxystearic acid, lithium hydroxide monohydrate and mineral oil. Complex soap greases are also in common use and comprise metal salts of a mixture of organic acids. One typical complex soap grease found in use today is a complex lithium soap grease prepared from 12-hydroxystearic acid, lithium hydroxide monohydrate, azelaic acid and mineral oil. The lithium soaps are described and exemplified in many patents including U.S. Pat. No. 3,758,407 (Harting), which issued on Sep. 11, 1973; U.S. Pat. No. 3,791,973 (Gilani), which issued on Feb. 12, 1974; and U.S. Pat. No. 3,929,651 (Murray), which issued on Dec. 30, 1975, all of which are incorporated herein by reference together with U.S. Pat. No. 4,392,967 (Alexander), which issued on Jul. 12, 1983.

A description of the additives used in greases may be found in Boner, "Modern Lubricating Greases", 1976, Chapter 5, which is incorporated herein by reference, as well as additives listed above in the other products.

COMPRESSOR OILS

The polyol ester composition can be used in the formulation of compressor oils together with selected lubricant additives. The preferred compressor oil is typically formulated using the polyol ester composition formed according to the present invention together with any conventional compressor oil additive package. The additives listed below are typically used in such amounts so as to provide their normal attendant functions. The additive package may include, but is not limited to, oxidation inhibitors, additive solubilizers, rust inhibitors/metal passivators, demulsifying agents, and anti-wear agents.

The compressor oil according to the present invention can employ typically about 80 to 99% base stock and about 1 to 15% solvent, with the remainder comprising an additive package.

The additives for compressor oils are also set forth in U.S. Pat. No. 5,156,759 (Culpon, Jr.), which issued on Oct. 20, 1992, and which is incorporated herein by reference.

GEAR OILS

The polyol ester composition can be used in the formulation of gear oils together with selected lubricant additives. The preferred gear oil is typically formulated using the polyol ester composition formed according to the present invention together with any conventional gear oil additive package. The additives listed below are typically used in such amounts so as to provide their normal attendant functions. The additive package may include, but is not limited to, antifoaming agents, antioxidants, extreme pressure agents, antiwear agents, rust inhibitors, corrosion inhibitors, demulsifiers, friction modifiers, dispersants, pour-point depressants, and viscosity modifiers.

It is extremely important in many lubricant applications such as aircraft turbine oils to provide a lubricant product which is thermally/oxidatively stable. One means of measuring relative thermal/oxidative stability in lubricants is via high pressure differential scanning calorimetry (HPDSC). In this test, the sample is heated to a fixed temperature and held there under a pressure of air (or oxygen) and the time to onset of decomposition is measured. The longer the time to decomposition, the more stable the sample. In all cases described hereafter, the conditions are as follows unless specifically noted otherwise: 220° C., 3.445 MPa (500 psi) air (i.e., 0.689 MPa (100 psi) oxygen and 2.756 MPa (400 psi)nitrogen), and the addition of 0.5 wt. % dioctyl diphenyl amine (Vanlube-81®) as an antioxidant.

EXAMPLE 1

For comparative purposes, Table 1 below demonstrates the enhanced thermal/oxidative performance of polyol ester compositions which do not have unconverted hydroxyl groups disposed about the carbon chain thereof versus conventional non-polyol esters.

TABLE 1

| Sample Number | Ester | HPDSC Decomposition Time, Min. |
|---|---|---|
| 1 | TMP/C$_7$/C$_9$/TMH | 23.9 |
| 2 | TMP/C$_7$/C810 | 23.4 |
| 3 | Diisoheptyl Adipate | 11.6 |
| 4 | Diisooctyl Adipate | 9.7 |
| 5 | Diisodecyl Adipate | 6.0 |
| 6 | Ditridecyl Adipate | 3.9 |
| 7 | Diisooctyl Phthalate | 8.0 |
| 8 | Ditridecyl Phthalate | 10.2 |

TMP denotes trimethylol propane.
C$_7$ is a linear C$_7$ acid.
C$_9$ is a linear C$_9$ acid.
TMH is 3,5,5-trimethyl hexanoic acid.
C810 is a mixture of 3–5 mole % n-C$_6$ acid, 48–58 mole % n-C$_8$ acid, 36–42 mole % n-C$_{10}$ acid, and 0.5–1.0 mole % n-C$_{12}$ acid.

The data set forth below in Table 2 indicate that there is considerable room for improving the thermal/oxidative performance of polyol esters as measured by the HPDSC test. In particular, it should be noted that esters of 3,5,5-trimethyl hexanoic acid and 2,2-dimethylpropionic acid (i.e., neopentanoic (neoC$_5$)) are particularly stable under the HPDSC test.

TABLE 2

| Sample Number | Ester | HPDSC Decomposition Time, Min. |
|---|---|---|
| 9 | TMP/n-C$_9$ | 14.2 |
| 10 | TechPE/n-C$_9$ | 14.7 |
| 11 | TMP/TMH | 119 |
| 12 | TechPE/TMH | 148 |
| 13 | MPE/TMH | 143 |

TABLE 2-continued

| Sample Number | Ester | HPDSC Decomposition Time, Min. |
|---|---|---|
| 14 | TMP/n-C$_5$ | 51.9 |
| 15 | 50% TMP/TMH and 50% TMP/n-C$_5$ | 65.7 |
| 16 | MPE/TMH/neo-C$_5$ | 168 | n-C$_9$ is a linear normal C$_9$ acid.
TechPE is technical grade pentaerythritol (i.e., 88% mono-, 10% di- and 1–2% tripentaelythritol).
MPL is mono-pentaerythritol.
n-C$_5$ is a linear normal C$_5$ acid.
TMH is 3,5,5-trimethyl hexanoic acid.
neo-C$_5$ is 2,2-dimethyl propionic acid.

A polyol ester having unconverted hydroxyl groups disposed thereon was formed using technical grade pentaerythritol and 3,5,5-trimethyl hexanoic acid (Sample 18) by mixing about 3.25 % molar equivalents of 3,5,5-trimethyl hexanoic acid with each mole of technical grade pentaerythritol. This was compared in Table 3 below with a conventional polyol ester formed from technical grade pentaerythritol and 3,5,5-trimethyl hexanoic acid (Sample 17) prepared using an excess of 3,5,5-trimethyl hexanoic acid.

TABLE 3

| Sample Number | Ester | Hydroxyl Number | HPDSC Decomposition Time, Min. |
|---|---|---|---|
| 17 | TechPE/TMH | <5 | 148 |
| 18 | TechPE/TMH w/25% uncon. OH | 83 | 468 |

TechPE is technical grade pentaerythritol (i.e., about 88% mono-, 10% di- and 1–2% tri-pentaerythritol).
TMH is 3,5,5-trimethyl hexanoic acid.

The data set forth above in Tables 1–3 support the discovery by the present inventors that certain compositions of polyol esters which include unconverted hydroxyl (OH) groups have surprisingly enhanced thermal/oxidative stability as measured by high pressure differential scanning calorimetry (HPDSC) versus conventional polyol and non-polyol esters.

EXAMPLE 2

The data set forth below in Table 4 demonstrate that polyol ester compositions having unconverted hydroxyl groups which are formed from polyols and branched acids in accordance with the present invention exhibit internal antioxidant properties.

TABLE 4

| Sample Number | Ester | Hydroxyl Number | HPDSC Decomposition Time, Min. | Unconverted Hydroxyl Groups (mole %) |
|---|---|---|---|---|
| 1 | TechPE/TMH | greater than 50 | 468* | greater than 15.3 |
| 2 | TechPE/TMH | greater than 50 | 58.3 no V-81 | greater than 15.3 |
| 3 | TechPE/L9 | less than 5 | 16.9* | less than 2.6 |
| 4 | Tech PE/TMH | less than 5 | 148* | less than 2.6 |
| 5 | Tech PE/TMH | less than 5 | 3.14 no V-81 | less than 2.6 |

*Ester with 0.5% V-81
V-81 is dioctyl diphenylamine.
TechPE is technical grade pentaerythritol (i.e., 88% mono-, 10% di- and 1–2% tri-pentaerythritol).
TMH is 3,5,5-trimethyl hexanoic acid.
L9 is blend of 62–70 mole % linear C$_9$ acid and 30–38 mole % branched C$_9$ acid.

The results in Table 4 above demonstrate that polyol esters with unconverted hydroxyl groups (i.e., sample numbers 1 and 2) greatly enhance the oxidative induction time of the lubricant formulation versus conventional polyol esters which do not have any significant amount of free or unconverted hydroxyl groups. Moreover, combining these unique polyol esters with an antioxidant such as V-81 significantly extends the time required for decomposition (see sample no. 1). Although the time for decomposition was reduced when this polyol ester did not include any added antioxidant, it still took approximately 3½ times longer to decompose versus a conventional C$_9$ acid polyol ester which had an antioxidant additive (i.e., 58.3 minutes (sample 2) versus 16.9 minutes (sample 3)). Furthermore, Samples 4 and 5 demonstrate that decomposition of the polyol ester compositions having a hydroxyl number less than 5 occurs much more rapidly compared to polyol ester compositions of the same acid and polyol having a hydroxyl number greater than 50 (e.g., Samples 1 and 2) regardless of whether or not an antioxidant is admixed with the respective polyol ester composition. This clearly demonstrates that synthesizing a polyol ester composition having unconverted hydroxyl groups disposed about the carbon chain of the polyol ester provides enhanced thermal/oxidative stability to the resultant product, as measured by HPDSC. Finally, a comparison of Sample Nos. 2 and 5, wherein no antioxidant was used, clearly establishes the antioxidant properties of the polyol ester of technical grade pentaerythritol and 3,5,5-trimethyl hexanoic acid having substantial amounts of unconverted hydroxyl group bonded which has an HPDSC of 58.3 minutes versus the same polyol ester with little or no unconverted hydroxyl groups which has an HPDSC of 3.14 minutes.

FIG. 1 demonstrates that increases in induction time also result on polyol esters made with linear carboxylic acids as hydroxyl number increases. The ester is the product of trimethylolpropane and linear C$_7$, C$_8$ and C$_{10}$ acids.

EXAMPLE 3

The following complex acid esters were prepared wherein the hydroxyl number was adjusted between full and partial esters. From the data set forth below in Table 5, it can be seen that for HPDSC improved benefits were observed relative to complex acid esters with hydroxyl numbers of approximately 5.

TABLE 5

| Complex Acid Ester | OH Number (mg KOH/g) | HPDSC (min.) |
|---|---|---|
| TMP + adipic acid + TMH | 4.77 | 29.30 |
| TMP + adipic acid + TMH | 43.50 | 61.07 |
| TMP + adipic acid + TMH | 65.20 | 75.53 |

TABLE 5-continued

| Complex Acid Ester | OH Number (mg KOH/g) | HPDSC (min.) |
|---|---|---|
| TPE + adipic acid + TMH | 6.58 | 35.96 |
| TPE + adipic acid + TMH | 27.28 | 79.49 |
| TPE + adipic acid + TMH | 61.52 | 105.97 |

TMP denotes trimethylol propane
TPE denotes technical grade pentaerythritol
THM is 3,5,5-trimethyl hexanoic acid.

EXAMPLE 4

Comparative deposits tests were made on two aircraft turbine oils where the key difference was the hydroxyl number of the synthetic polyol ester base stock. The conventional aircraft turbine oil utilized a base stock with a hydroxyl number of well below 3, while the aircraft turbine oil formulated using the higher hydroxyl polyol ester base stock of the present invention exhibited a hydroxyl number ranging from 4.1 to 7.3. Thermal oxidative stability was examined using the Inclined Panel Deposit Test (IPDT) and Vapor Phase Coker (VPC).

The IPDT is a tool for predicting the deposit forming characteristics of aircraft turbine, engine lubricants (but, in fact, has much broader application). During the test, oil is dripped onto a heated metal panel at 304° C. (580° F.). The panel is held at a 4° angle during the test. The test oil flows over the panel at 60 mls/hr, while moist air sweeps across at 12 liters per hour. The used oil collects in a sump and is continuously recirculated (for 24 hours) using a positive displacement pump.

At the end of the IPDT procedure, the amount and type of deposit on the panel is determined. A rating scale is used to determine the deposit forming tendency of the oils. The area of each type of deposit is measured and multiplied by the appropriate demerit factor. The total number of demerits obtained is then divided by the total area of deposits (oil wetted area) to obtain the deposit demerit rating. Demerit factors run from a low number for a lightly varnished surface to a high number for blistered or flaked carbon. The latter is significant since it can break off in an engine and could clog filters or other equipment. Therefore, the lower the rating either the less likelihood there is of an undesirable deposit or the cleaner a panel appears to be. In addition, the stressed oil is examined for changes in viscosity and acidity.

For the VPC test, air is bubbled through a pot of aircraft turbine oil held at 204° C. (400° F.), an oil mist is carried off the pot through a heated zone where the controller temperature is set at 371 ° C. (700° F.). The amount of deposit formed in the heated zone and the condition of the oil in the pot is then analyzed at the end of 18 hours.

The results, summarized in Tables 6 and 7 below, show the improved cleanliness with the aircraft turbine oil (ATO) formed from a polyol ester base stock having unconverted hydroxyl groups (i.e., a high hydroxyl ATO) according to the present invention versus the conventional aircraft turbine oil formed from a fully esterified polyol ester base stock.

TABLE 6

(Inclined Panel Deposit Tests at 304° C.)

| ATO Type | High Hydroxyl ATO | Low Hydroxyl ATO |
|---|---|---|
| OH Numbers | 4.1–7.3 | less than 3 |
| OH Conversion, % | 99.0–98.2 | 99.7 |
| Number of Date Points | 6 | 2 (8)* |
| Average Rating | 3.73 | 475 (43)* |
| Average Final Viscosity (cSt) | 73.8 | 52.7 (67.1)* |
| Average Final TAN** | 15.6 | 11.0 (16.9)* |
| Deposit Weight, grams | 0.33 | 0.35 |

*Two data points run at same time as high hydroxyl ATO, while the other eight data points on base stocks with OH numbers less than 3 were run during the prior three months.
**TAN designates Total Acid Number.

TABLE 7

(Vapor Phase Coker)

| ATO Type | High Hydroxyl ATO | Low Hydroxyl ATO |
|---|---|---|
| OH Numbers | 5.4 | 1.1 |
| OH Conversion, % | 98.6 | 99.7 |
| Oil Loss, grams | 10.6 | 10.5 |
| Deposit Weight, mg | 144 | 194 |
| Final Viscosity (cSt) | 27.7 | 27.6 |
| Final TAN | 0.4 | 0.4 |

A full point improvement in panel rating was achieved with the ATO made with the higher hydroxyl number base stock according to the present invention. The data also suggested a mechanism for the improved cleanliness. Stressed oil from the higher hydroxyl number ATO had a higher viscosity than oil from the low hydroxyl ATO (i.e., ATO formed from fully esterified polyol ester base stocks). The partially converted esters of the present invention may be reacting with radicals, allowing them to remain soluble in the oil rather than dropping out as a deposit. As a result of these heavier species in the ATO, the viscosity of the ATO increases. This further illustrates the importance of the critical hydroxyl number range recited in the high hydroxyl polyol esters of the present invention. Viscosity increase on used oil is limited in some applications by equipment (such as pumps). Therefore, there are limits imposed on the preferred hydroxyl number range.

As demonstrated above in Table 7, vapor phase deposit weight for the higher hydroxyl aircraft turbine oil was lower than the deposit weight of the low hydroxyl or nearly fully esterified aircraft turbine oil.

EXAMPLE 5

Figure 2:
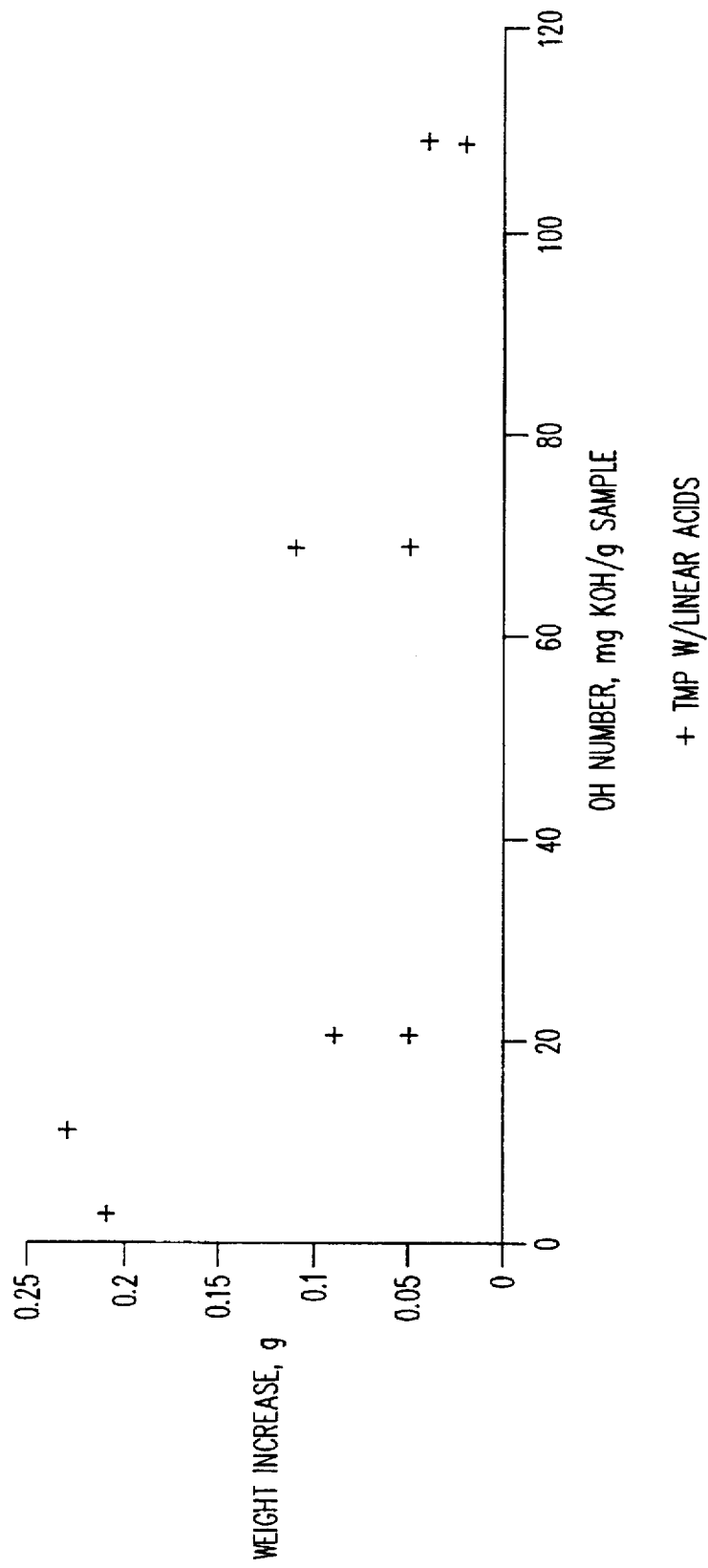
FIG. 2 is graph demonstrating the impact of hydroxyl number with Inclined Panel Deposit Test (IPDT) on weight change.
Figure 3:
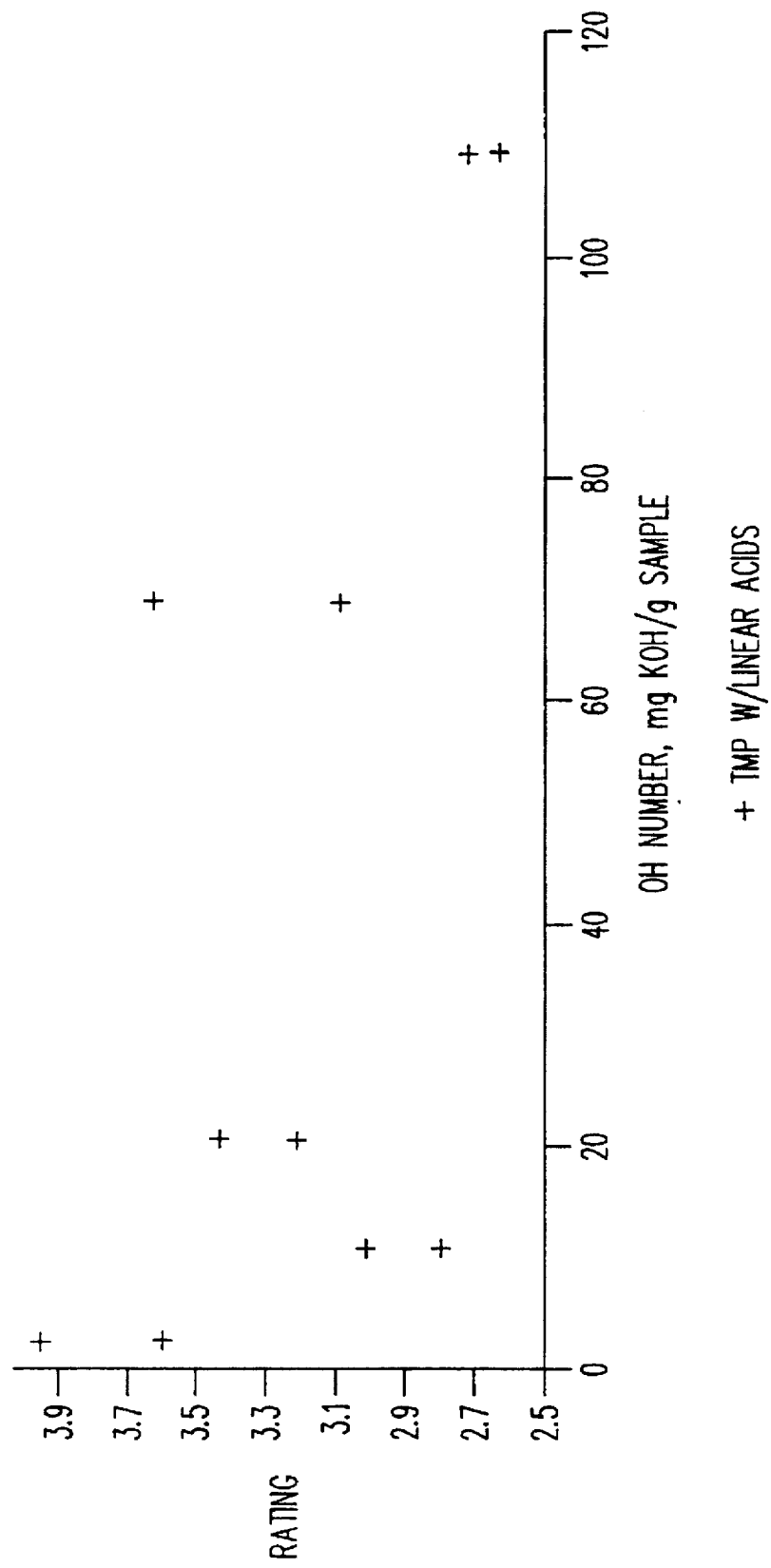
FIG. 3 is a graph demonstrating the impact of hydroxyl number with IPDT on rating.

The data in FIG. 2 demonstrates the dramatic impact which higher hydroxyl number polyol ester base stock have on weight increase using an inclined panel deposit test (IPDT). The higher the weight increase the more sediment and metals which a lubricant leaves as a deposit. Higher weight increases due to such deposits are extremely undesirable. Base stocks utilizing trimethylolpropane (TMP) and linear acids ($C_6$, $C_7$, $C_8$, $C_{10}$) of varying hydroxyl numbers was combined with an antiwear additive, metal passivator, and antioxidants. These formulated oils were run on the IPDT in duplicate at 293° C. The present inventors have shown in FIG. 2 that polyol esters formed from trimethylolpropane and linear $C_7$, $C_8$ and $C_{10}$ acids exhibit an unexpected reduction in weight increase as the hydroxyl number thereof exceeds 5. That is, polyol esters of the present invention show an improved cleanliness with linear acid based polyol esters over broad hydroxyl numbers. FIG. 3 indicates that there is a substantial improvement in rating with just a small increase in hydroxyl number over highly converted polyol esters (i.e., esters with a hydroxyl number less than 5).

EXAMPLE 6

Tests of corrosion and oxidative stability of light oils (OC&S) were conducted on ATO's having a range of hydroxyl numbers. The general test procedure is outlined in the Federal Test Method Standard 791C Method 5308.7. As described in the procedure, metal specimens are suspended in a measured amount of lubricant. The oil, at an elevated temperature, is blown with air for a period of time. When the test is completed, the oil is tested (for viscosity change, sediment formation, and oil loss) to determine the extent of degradation.

Two base stocks with a range of hydroxyl numbers were prepared for OC&S testing. One was made with technical grade pentaerythritol (TPE) and linear ($C_5$, $C_6$, $C_7$, $C_8$, and $C_{10}$ acids) and one branched (3,5,5-trimethylhexanoic acid) acid and is used as a 5 cSt turbine oil. The other base stock utilized trimethylolpropane (TMP) and linear acids ($C_6$, $C_7$, $C_8$, and $C_{10}$) and is a 4 cSt oil used as a base stock in a turbine oil.

These base stocks were each formulated with 0.5 wt. % of phenothiazine (i.e., an antioxidant) and run for 48 hours at 425° F. (218° C.).

A total of twelve runs were made over ranges of hydroxyl numbers (i.e., hydroxyl numbers of 2–215 for the TPE ester oil and from 2.8–108.9 for the TMP ester oil. All the results are set forth in Tables 8 and 9 below:

TABLE 8

(TPE ESTER OILS)

| | Sample No. | | | | | |
|---|---|---|---|---|---|---|
| | 1 | 2 | 3 | 4 | 5 | 6 |
| Polyol | TPE | TPE | TPE | TPE | TPE | TPE |
| OH# | 2 | 17.4 | 21.8 | 40.1 | 170 | 215 |
| Approximate OH Conver., % | 99.5 | 96 | 95 | 91 | 65 | 56 |
| Viscosity Change, % | 38.35 | 41.16 | 35.2 | 51.31 | 35.77 | — |
| Evaporation Loss, % | 3.8 | 3.4 | 3.95 | 4.7 | 6.3 | 8.2 |
| Δ TAN | 2.94 | 4.12 | 1.69 | 3.03 | 8.13 | 9.8 |
| Sediment, mg | 218 | 44.6 | 21.8 | 9.9 | 3060.5 | 6594.4 |
| Viscosity at 100° F. cSt | | | | | | |
| Initial | 25.97 | 27.65 | 28.07 | 29.86 | 75.07 | 61.02 |
| Final | 35.93 | 39.03 | 37.95 | 45.18 | 102.67 | * |
| Test Cell Appearance | (a) | (b) | (c) | (d) | (e) | (f) |

*Sample would not filter.
(a) denotes a heavy stain at interface with black deposits.
(b) denotes a moderate stain at air/oil interface.
(c) denotes moderately stained.
(d) denotes lightly stained.
(e) denotes moderately stained.
(f) denotes ring at interface with heavy black deposits.

TABLE 9

(TMP ESTER OILS)

| | Sample No. | | | | | |
|---|---|---|---|---|---|---|
| | 7 | 8 | 9 | 10 | 11 | 12 |
| Polyol | TMP | TMP | TMP | TMP | TMP | TMP |
| OH# | 2.8 | 10.9 | 20.7 | 44.0 | 68.9 | 108.9 |
| Approximate OH Conver., % | 99.2 | 97 | 94 | 89 | 82 | 72 |
| Viscosity Change, % | 43.3 | 41.48 | 42.23 | 272.53 | 22.05 | 6.8 |
| Evaporation Loss, % | 2.9 | 2.8 | 3.9 | 4.14 | 4.45 | 5.7 |
| Δ TAN | 8.21 | 7.38 | 5.52 | 7.24 | 3.79 | 4.65 |
| Sediment, mg | 261.8 | 38.8 | 9.3 | 2527 | 3385 | 4166 |
| Viscosity at 100° F. cSt | | | | | | |
| Initial | 18.87 | 18.37 | 19.63 | 20.68 | 22.36 | 25.29 |
| Final | 27.04 | 25.99 | 27.92 | 27.04 | 27.29 | 27.01 |
| Test Cell Appearance | (g) | (h) | (i) | (j) | (k) | (l) |

(g) denotes moderately stained heavy ring at air/oil interface with black deposits.
(h) denotes moderately stained ring at air/oil interface, some black deposits.
(i) denotes moderately stained.
(j) denotes moderate stained ring at air/oil interface.
(k) denotes light stains with ring at air/oil interface.
(l) denotes lightly stained with chunks of black deposits.

Figure 4:
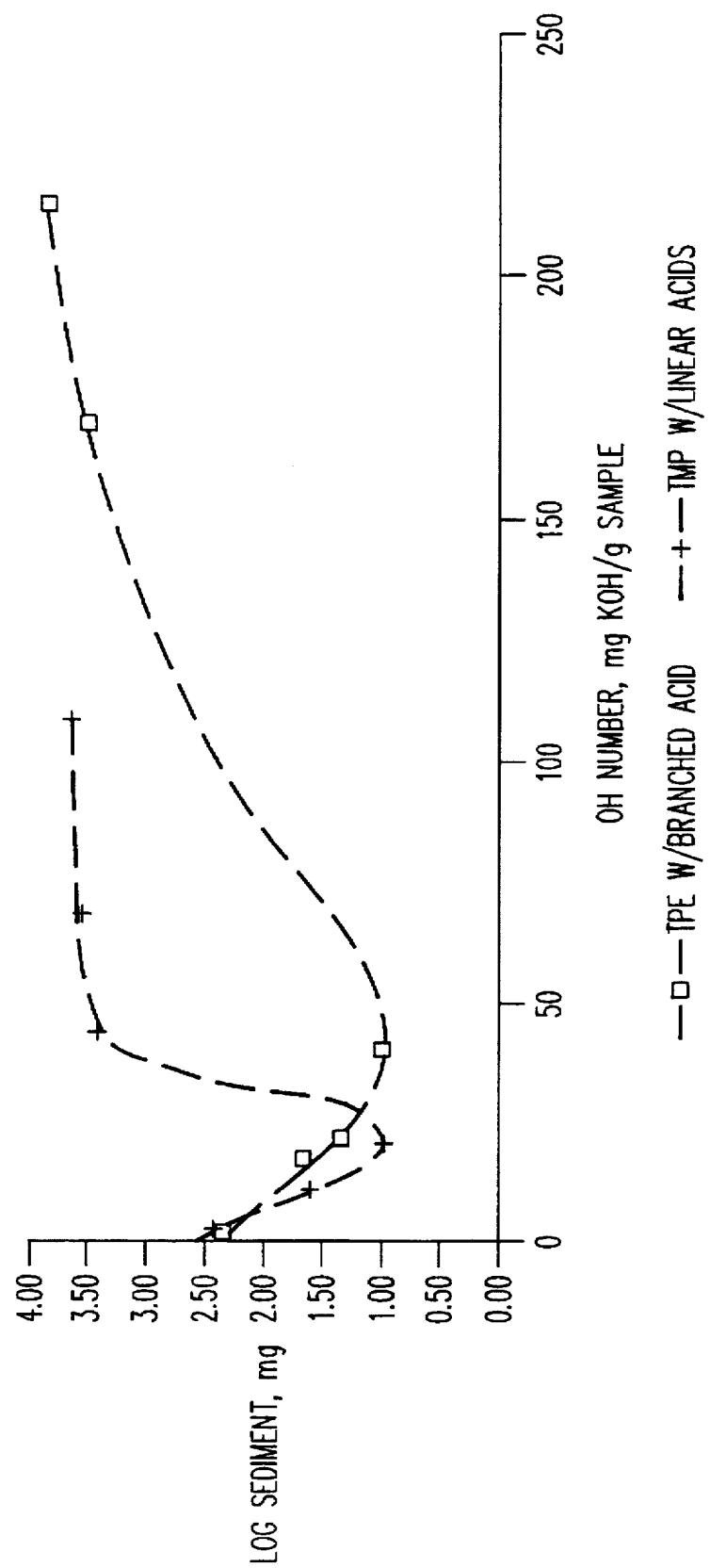
FIG. 4 is a graph plotting Log sediment versus hydroxyl number using the OC&S Test at 425° F. (218° C.) for 48 hours in the presence of 0.5 wt. % phenothiazine.

It is preferred that the hydroxyl number of the polyol ester is not too high in order to avoid sediment formation; however, where sediment formation could be controlled by incorporating additives, then hydroxyl numbers up to 180 may be acceptable for certain applications. Increased sediment formation would require the oil formulator to add costly antioxidants and/or corrosion inhibitors to overcome the negative impact of these higher hydroxyl number oils A closer look at the lower hydroxyl numbers using a semi-log plot (FIG. 4) illustrates the optimum achieved by operating with a base stock having an intermediate hydroxyl number level. In the range of about greater than 5 to 100 and more preferably 10 to 80 hydroxyl number for these esters, a minimum amount of sediment is produced. The mechanism is likely that as hydroxyl number increases, the unconverted ester reacts with radicals and keeps them in solution. However, as the corrosion of metal coupons in the OC&S test occurs at higher hydroxyl numbers more sediment is formed effectively obscuring the antioxidant effect. It is also worth noting that the optimum in performance is also apparent from the appearance of the cell at the end of the test.

Viscosity change across the range of hydroxyl number is relatively flat except for a single point. Again, if the sediment had not increased (due to corrosion products and heavies falling out of the oil) so rapidly, one would expect the viscosity of the oil to have increased.

Figure 5:
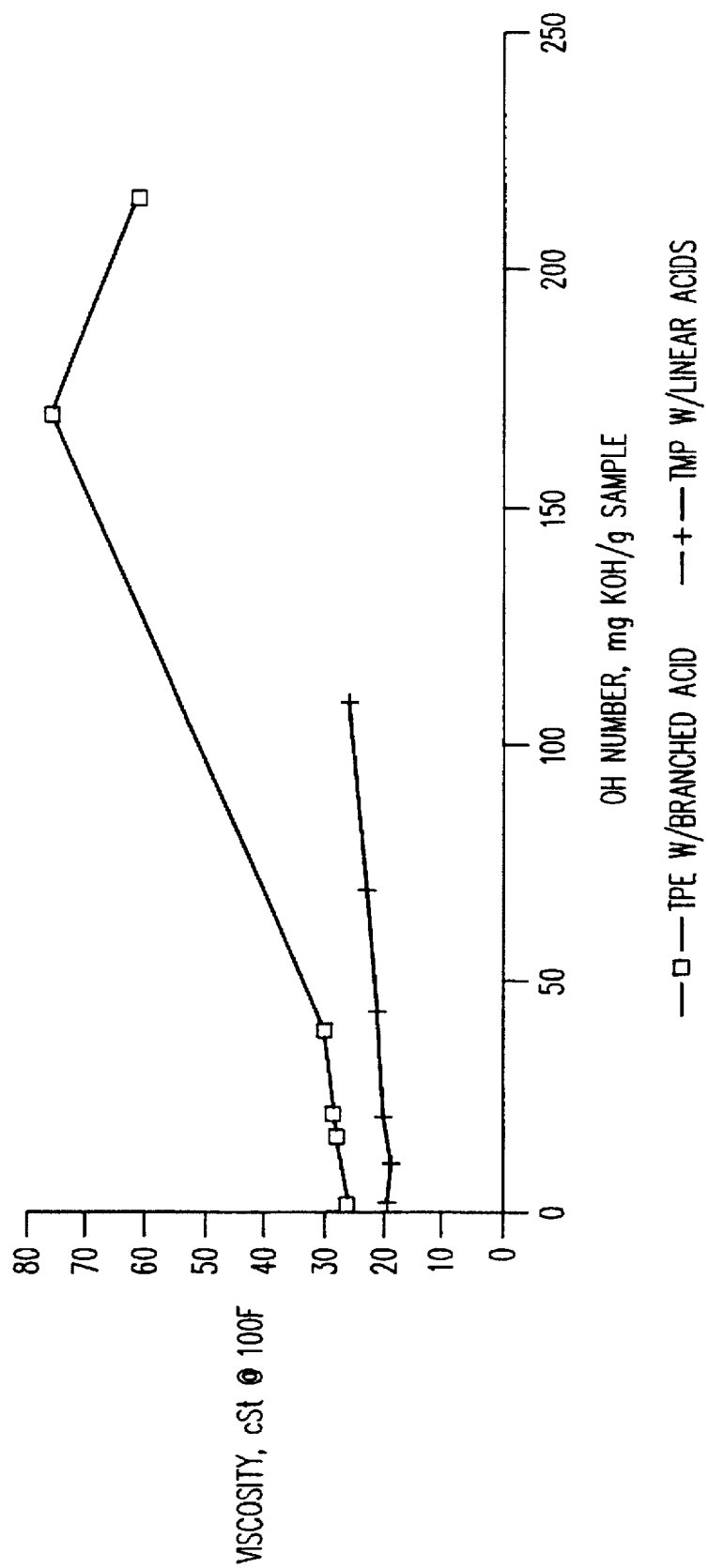
FIG. 5 is a graph plotting viscosity at 100° F. (38° C.) on fresh oil versus hydroxyl number.

There are two more potentially negative aspects of operating at too high a hydroxyl number. The volatility loss on the OC&S test increases significantly. Also, the viscosity on the fresh oil increases significantly (especially when branched acids are involved) with increasing hydroxyl numbers (see FIG. 5). This would imply that it could be more difficult to hit narrow viscosity ranges set by specifications for commercial products as manufacturers attempt to make higher hydroxyl number base stocks.

EXAMPLE 7

Data set forth below in Table 10 demonstrate that polyol esters with unconverted hydroxyl groups (i.e., unconverted hydroxyl groups) formed from polyols and branched acids according to the present invention are also capable of enhancing the thermal/oxidative stability when blended with other hydrocarbon base stocks such as poly alpha olefins (PAO).

TABLE 10

| Sample Number | Base Stock Composition | Hydroxyl Number* | HPDSC Decomposition Time, Min.** |
|---|---|---|---|
| 1 | PAO6 | | 10.65 |
| 2 | 95% PAO6 and 5% TMP/7810 | <5 | 12.99 |
| 3 | 90% PAO6 and 10% TMP/7810 | <5 | 13.49 |
| 4 | 75% PAO6 and 25% TMP/7810 | <5 | 18.30 |
| 5 | 95% PAO6 and 5% TechPE/TMH | <5 | 12.89 |
| 6 | 90% PAO6 and 10% TechPE/TMH | <5 | 13.52 |
| 7 | 75% PAO6 and 25% TechPE/TMH | <5 | 17.03 |
| 8 | 95% PAO6 and 5% MPE/2EH | 63.8 | 18.19 |
| 9 | 90% PAO6 and 10% MPE/2EH | 63.8 | 28.75 |
| 10 | 95% PAO6 and 5% MPE/TMH | 68.5 | 22.57 |
| 11 | 90% PAO6 and 10% MPE/TMH | 68.5 | 53.68 |
| 12 | 75% PAO6 and 25% MPE/TMH | 68.5 | 108.86 |

PAO6 is a 1-decene oligomer.
*Hydroxyl Number is measured in mg KOH/gram sample and is the hydroxyl number of the ester-containing portion of the blend.
**Denotes that the HPDSC measurement was conducted at 190° C. and 3.445 MPa in the presence of 0.5% Vanlube ®-81 additive (i.e., dioctyl diphenyl amine).
2EH is 2 ethyl hexanoic acid.
TechPE is technical grade pentaerythritol (i.e., 88% mono-, 10% di- and 1–2% tri-pentaerythritol).
MPE is mono-pentaerythritol.
TMH is 3,5,5-trimethyl hexanoic acid.
TMP is trimethylol propane.
7810 is a blend of 37 mole % of a n-C$_7$ acid and 63 mole % of a mixture of 3–5 mole % n-C$_6$ acid, 48–58 mole % n-C$_8$ acid, 36–42 mole % n-C$_{10}$ acid, and 0.5–1.0 mole % n-C$_{12}$ acid.

The results set forth above in Table 10 demonstrate that polyol ester compositions with unconverted hydroxyl content (i.e., sample numbers 8–12) bring about enhanced thermal/oxidative stability as measured by HPDSC when blended with hydrocarbon base stocks such as poly alpha olefins.

EXAMPLE 8

Data set forth below in Table 11 demonstrate that polyol esters with unconverted hydroxyl groups formed from polyols and branched acids according to the present invention and which have been admixed with 0.5% Vanlube® 81 (an antioxidant) are capable of retarding the onset of thermal/oxidative degradation as measured by HPDSC. The below samples were run at 3.445 MPa (500 psi) air (i.e., 0.689 MPa (100 psi) oxygen and 2.756 MPa (400 psi) nitrogen).

TABLE 11

| Sample | Hydrocarbon | Ester | Ratio | Temp. (°C.) | Hydroxyl Number | HPDSC (minutes) |
|---|---|---|---|---|---|---|
| 1 | SN150 | MPE/2EH | 95/5 | 190 | 63.5 | 14.53 |
| 2 | SN150 | MPE/2EH | 90/10 | 190 | 63.5 | 22.41 |
| 3 | SN150 | MPE/2EH | 75/25 | 190 | 63.5 | 31.94 |
| 4 | SN150 | MPE/TMH | 95/5 | 190 | 68.5 | 16.98 |
| 5 | SN150 | MPE/TMH | 90/10 | 190 | 68.5 | 17.58 |
| 6 | SN150 | MPE/TMH | 75/25 | 190 | 68.5 | 57.18 |

SN150 is a low sulfur, neutralized, saturated, linear hydrocarbon fluid having between 14 to 34 carbon atoms.
TMH is 3,5,5-trimethyl hexanoic acid.
2EH is 2-ethyl hexanoic acid.
MPE is monopentaerythritol TABLE 11-continued

| Sample | Hydrocarbon | Ester | Ratio | Temp. (°C.) | Hydroxyl Number | HPDSC (minutes) |
|---|---|---|---|---|---|---|

*hydroxyl number is measured in mg KOH/gram sample and is the hydroxyl number of the ester-containing portion of the blend.

EXAMPLE 9

The below esters all formed with 3,5,5-trimethylhexanoic acid (TMH) show improved performance. For example, the mono-hydroxyl pentaerythritol having a significant level of unreacted hydroxyl groups exhibited the lowest level of friction (i.e., 0.115) and wear volume (i.e., 1.35) versus other fully esterified synthetic esters. The formulations were tested in a Falex Block-on-Ring (BOR) tribometer at 100° C. with a 220 lb. load, a speed of 420 rpm (0.77 m/s), and a two hour test length. Friction coefficients are reported as end of run value. The end of run values show relative standard deviations (1$\sigma$) of approximately 1.5% Following the testing, wear volumes are determined by multiple scan profilometry. For a Superflo QC sample the relative standard deviation (1$\sigma$) is approximately 12%. The results are set forth below in Table 12:

TABLE 12

| Ester | End Friction | Wear Volume |
|---|---|---|
| Diester | 0.1245 | 2.35 |
| Phthalate | 0.1195 | 2.00 |
| Trimellitate | 0.1175 | 2.65 |
| Technical grade pentaerythritol ester | 0.1180 | 2.10 |
| Trimethylolpropane ester | 0.1180 | 2.75 |
| Technical grade pentaerythritol ester w/ unconverted (OH) | 0.1150 | 1.35 |

The unique polyol esters having unconverted hydroxyl groups according to the present invention have also been shown to exhibit high polarity which the present inventors have found to be very important in reducing friction and wear effects in crack case engines.

The novel polyol ester having unconverted hydroxyl groups according to the present invention also exhibits greatly enhanced fuel savings versus either no ester additive or fully esterified synthetic esters. The percent fuel savings is typically on the order of 2 to 2.5% for 5W40 oils, as measured by the Sequence VI Screener Test. The percent fuel savings will vary along with the viscosity of the oils tested.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A synthetic ester composition exhibiting increased thermal and oxidative stability versus fully esterified compositions, said synthetic ester composition comprises the reaction product of:

a branched or linear alcohol having the general formula R(OH)$_n$, wherein R is an aliphatic or cyclo-aliphatic group having from about 2 to 20 carbon atoms and n is at least 2; and at least one linear acid which has a carbon number in the range between about C$_5$ to C$_{20}$ or a mixture thereof with a $C_{12}$ linear acid; wherein said synthetic ester composition has a hydroxyl number of between about greater than 5 to 100.

2. The synthetic ester composition according to claim 1 wherein said synthetic ester composition a hydroxyl number of between about 10 to 80.

3. The synthetic ester composition according to claim 1 further comprising an antioxidant in an amount between about 0 to 8 wt. %, based on said synthetic ester composition.

4. The synthetic ester composition according to claim 1 wherein said branched or linear alcohol is selected from the group consisting of: neopentyl glycol, 2,2-dimethylol butane, trimethylol ethane, trimethylol propane, trimethylol butane, mono-pentaerythritol, technical grade pentaerythritol, di-pentaerythritol, tri-pentaerythritol, ethylene glycol, propylene glycol, polyalkylene glycols, 1,4-butanediol, 1,3-propanediol, and glycerol.

5. The synthetic ester composition according to claim 1 wherein said linear acid is at least one acid selected from the group consisting of: n-pentanoic acid, n-hexanoic, n-heptanoic acid, n-octanoic acid, n-nonanoic acid, and n-decanoic acid.

6. The synthetic ester composition according to claim 1 further comprises a polybasic acid, thereby forming a complex acid ester.

7. The synthetic ester composition according to claim 1 further comprising a polybasic acid and a second mono alcohol, thereby forming a complex alcohol ester.

8. The synthetic ester composition according to claim 1 further comprising at least one branched acid which has a carbon number in the range between about $C_4$ to $C_{20}$.

9. The synthetic ester composition according to claim 8 wherein said branched acid is at least one acid selected from the group consisting of: 2,2-dimethyl propionic acid, neoheptanoic acid, neooctanoic acid, neononanoic acid, isohexanoic acid, neodecanoic acid, 2-ethyl hexanoic acid, 3,5,5-trimethyl hexanoic acid, isoheptanoic acid, isooctanoic acid, isononanoic acid and isodecanoic acid.

10. The synthetic ester compositions according to claim 1 wherein said synthetic ester comprises the reaction product of trimethylolpropane and a mixture of 3–5 mole % n-$C_6$ acid, 48–58 mole % n-$C_8$ acid, 36–42 mole % n-$C_{10}$ acid, and 0.5–1.0 mole % n-$C_{12}$ acid.

11. A lubricant oil which is prepared from:
at least one synthetic ester composition exhibiting increased thermal and oxidative stability versus fully esterified compositions, said synthetic ester composition comprises the reaction product of: a branched or linear alcohol having the general formula R(OH)$_n$, wherein R is an aliphatic or cyclo-aliphatic group having from about 2 to 20 carbon atoms and n is at least 2; and at least one linear acid which has a carbon number in the range between about $C_5$ to $C_{10}$ or a mixture thereof with a $C_{12}$ linear acid; wherein said synthetic ester composition has a hydroxyl number of between about greater than 5 to 100; and
a lubricant additive package.

12. The lubricant oil according to claim 11 wherein said synthetic ester composition has a hydroxyl number of between about 10 to 80.

13. The lubricant oil according to claim 11 further comprising an antioxidant in an amount between about 0 to 8 wt. %, based on said synthetic ester composition.

14. The lubricant oil according to claim 13 wherein said antioxidant is present in an amount of between about 001 to 5 wt. %, based on said synthetic ester composition.

15. The lubricant oil according to claim 11 wherein said branched or linear alcohol is selected from the group consisting of: neopentyl glycol, 2,2-dimethylol butane, trimethylol ethane, trimethylol propane, trimethylol butane, mono-pentaerythritol, technical grade pentaerythritol, di-pentaerythritol, tri-pentaerythritol, ethylene glycol, propylene glycol, polyalkylene glycols, 1,4-butanediol, 1,3-propanediol, and glycerol.

16. The lubricant oil according to claim 11 wherein said linear acid is at least one acid selected from the group consisting of: n-pentanoic acid, n-hexanoic, n-heptanoic acid, n-octanoic acid, n-nonanoic acid, and n-decanoic acid.

17. The lubricant oil according to claim 11 wherein said lubricant oil is a blend of said synthetic ester composition and at least one additional base stock selected from the group consisting of: mineral oils, highly refined mineral oils, alkylated mineral oils, poly alpha olefins, polyalkylene glycols, phosphate esters, silicone oils, diesters and polyol esters.

18. The lubricant oil according to claim 17 wherein said synthetic ester composition is blended with said additional base stocks in a ratio between about 99:1 to 1:99 wt. %.

19. The lubricant oil according to claim 11 wherein said additive package comprises at least one additive selected from the group consisting of: anti-foaming agents, anti-wear agents, corrosion inhibitors, hydrolytic stabilizers, metal deactivators, detergents, pour point depressants, viscosity improvers, viscosity index improvers, and oxidation inhibitors.

20. The lubricant oil according to claim 11 wherein said lubricant oil comprises about 55–100% by weight of said synthetic ester composition, about 0–30% by weight of a diluent, and about 0 to 15% by weight of said additive package.

21. The lubricant oil according to claim 11 wherein said synthetic ester composition further comprises a polybasic acid, thereby forming a complex acid ester.

22. The lubricant oil according to claim 11 wherein said synthetic ester composition further comprises a polybasic acid and a second mono alcohol, thereby forming a complex alcohol ester.

23. The lubricant oil according to claim 11 wherein said lubricant oil is one oil selected from the group consisting of: crankcase engine oils, two-cycle engine oils, catapult oils, hydraulic fluids, drilling fluids, turbine oils, greases, compressor oils, gear oils, and functional fluids.

24. The lubricant oil according to claim 23 wherein said turbine oil is an aircraft turbine oil.

25. The lubricant oil according to claim 11 further comprising a branched acid which has a carbon number in the range between about $C_4$ to $C_{20}$.

26. The lubricant oil according to claim 25 wherein said branched acid is at least one acid selected from the group consisting of: 2,2-dimethyl propionic acid, neoheptanoic acid, neooctanoic acid, neononanoic acid, isohexanoic acid, neodecanoic acid, 2-ethyl hexanoic acid, 3,5,5-trimethyl hexanoic acid, isoheptanoic acid, isooctanoic acid, isononanoic acid and isodecanoic acid.

27. The lubricant oil according to claim 11 wherein said branched or linear alcohol is trimethylolpropane and said linear acid is a mixture of 3–5 mole % n-$C_6$ acid, 48–58 mole % n-$C_8$ acid, 36–42 mole % n-$C_{10}$ acid, and 0.5–1.0 mole % n-$C_{12}$ acid.

28. A synthetic ester composition exhibiting increased thermal and oxidative stability versus fully esterified compositions, said synthetic ester composition comprises the reaction product of:

a branched or linear alcohol having the general formula $R(OH)_n$, wherein R is an aliphatic or cyclo-aliphatic group having from about 2 to 20 carbon atoms and n is at least 2; and at least one branched acid which has a carbon number in the range between about $C_4$ to $C_{20}$; wherein said synthetic ester composition has a hydroxyl number of between about greater than 5 to 100.

29. The synthetic ester composition according to claim 28 wherein said synthetic ester composition has a hydroxyl number of between about 10 to 80.

30. A lubricant oil which is prepared from:

at least one synthetic ester composition exhibiting increased thermal and oxidative stability versus fully esterified compositions, said synthetic ester composition comprises the reaction product of: a branched or linear alcohol having the general formula $R(OH)_n$, wherein R is an aliphatic or cyclo-aliphatic group having from about 2 to 20 carbon atoms and n is at least 2; and at least one branched acid which has a carbon number in the range between about $C_4$ to $C_{20}$; wherein said synthetic ester composition has a hydroxyl number of between about greater than 5 to 100; and a lubricant additive package.

31. The lubricant oil according to claim 30 wherein said synthetic ester composition has a hydroxyl number of between about 10 to 80.

32. The lubricant oil according to claim 30 wherein said lubricant oil is a blend of said synthetic ester composition and at least one additional base stock selected from the group consisting of: mineral oils, highly refined mineral oils, alkylated mineral oils, poly alpha olefins, polyalkylene glycols, phosphate esters, silicone oils, diesters and polyol esters.

33. The lubricant oil according to claim 30 wherein said lubricant oil is one oil selected from the group consisting of: crankcase engine oils, two-cycle engine oils, catapult oils, hydraulic fluids, drilling fluids, turbine oils, greases, compressor oils, gear oils, and functional fluids.

34. The lubricant oil according to claim 33 wherein said turbine oil is an aircraft turbine oil.

* * * * *

UNITED STATES PATENT AND TRADEMARK OFFICE
CERTIFICATE OF CORRECTION

PATENT NO.   : 5,698,502
DATED        : December 16, 1997
INVENTOR(S)  : Pafford et al.

It is certified that error appears in the above-identified patent and that said Letters Patent is hereby corrected as shown below:

<u>Column 22, claim 1,</u>
Line 67, delete "$C_{20}$" and insert -- $C_{10}$ --

Signed and Sealed this

Twenty-fifth Day of September, 2001

Attest:

*Attesting Officer*

NICHOLAS P. GODICI
*Acting Director of the United States Patent and Trademark Office*